(12) United States Patent
Fang et al.

(10) Patent No.: US 11,116,420 B2
(45) Date of Patent: Sep. 14, 2021

(54) MONITORING DISTANCE TO SELECTED ANATOMICAL STRUCTURES DURING A PROCEDURE

(71) Applicants: Biosense Webster (Israel) Ltd., Yokneam (IL); ACCLARENT, Inc., Irvine, CA (US)

(72) Inventors: Itzhak Fang, Irvine, CA (US); Noam Rachli, Hadera (IL); Yoav Pinsky, Bet Keshet (IL); Itamar Bustan, Zichron Ya'acov (IL); Jetmir Palushi, Irvine, CA (US); Zvi Dekel, Zichron Yaakov (IL)

(73) Assignees: BIOSENSE WEBSTER (ISRAEL) LTD., Yokneam (IL); ACCLARENT, INC., Irvine, CA (US)

( * ) Notice: Subject to any disclaimer, the term of this patent is extended or adjusted under 35 U.S.C. 154(b) by 794 days.

(21) Appl. No.: 15/854,472

(22) Filed: Dec. 26, 2017

(65) Prior Publication Data
US 2019/0192045 A1 Jun. 27, 2019

(51) Int. Cl.
*A61B 5/06* (2006.01)
*A61B 34/20* (2016.01)
(Continued)

(52) U.S. Cl.
CPC .............. *A61B 5/065* (2013.01); *A61B 5/062* (2013.01); *A61B 5/6886* (2013.01); *A61B 17/24* (2013.01); *A61B 34/20* (2016.02); *A61B 34/25* (2016.02); *A61B 1/233* (2013.01); *A61B 5/6819* (2013.01); *A61B 5/6852* (2013.01); *A61B 8/0841* (2013.01); *A61B 90/36* (2016.02);
(Continued)

(58) Field of Classification Search
CPC ....... A61B 5/065; A61B 5/6886; A61B 34/20; A61B 2034/105; A61B 2034/2051; A61B 8/0841
See application file for complete search history.

(56) References Cited

U.S. PATENT DOCUMENTS

| | | |
|---|---|---|
| 5,391,199 A | 2/1995 | Ben-Haim |
| 6,239,724 B1 | 5/2001 | Doron |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim |

(Continued)

FOREIGN PATENT DOCUMENTS

WO 96/05768 A1 2/1996

OTHER PUBLICATIONS

Bosscher P., & Heman, D., "Real-Time Collision Avoidance Algorithm for Robotic Manipulators", IEEE International Conference on Technologies for Practical Robot Applications, IEEE, 10 pgs., Nov. 2009.

*Primary Examiner* — Jason M Ip
(74) *Attorney, Agent, or Firm* — Volpe Koenig

(57) ABSTRACT

Physicians performing invasive procedures utilize instruments inserted into a human body to perform the procedures. Such procedures typically involve actions to be performed on specific targeted anatomical structures. During the procedure, nearby anatomical structures unrelated to the procedure should generally be avoided. A system and techniques are provided herein for monitoring the position of such unrelated nearby anatomical structures relative to one or more surgical instruments. The system emits a warning to a human operator such as a surgeon if one of the instruments is too close to a monitored anatomical structure.

20 Claims, 6 Drawing Sheets

(51) Int. Cl.
  *A61B 34/00* (2016.01)
  *A61B 5/00* (2006.01)
  *A61B 34/10* (2016.01)
  *A61B 17/24* (2006.01)
  *A61B 8/08* (2006.01)
  *A61B 90/00* (2016.01)
  *A61B 1/233* (2006.01)
  *A61B 17/00* (2006.01)
  *A61B 90/50* (2016.01)

(52) U.S. Cl.
  CPC ............... *A61B 2017/00119* (2013.01); *A61B 2034/105* (2016.02); *A61B 2034/2051* (2016.02); *A61B 2034/2068* (2016.02); *A61B 2090/372* (2016.02); *A61B 2090/502* (2016.02)

(56) References Cited

U.S. PATENT DOCUMENTS

| | | |
|---|---|---|
| 2002/0065444 A1 | 5/2002 | Deckman et al. |
| 2002/0065455 A1 | 5/2002 | Ben-Haim et al. |
| 2003/0120150 A1 | 6/2003 | Govari et al. |
| 2004/0068178 A1 | 4/2004 | Govari |
| 2006/0092165 A1* | 5/2006 | Abdalla ............... G06F 12/126 345/545 |
| 2010/0312095 A1* | 12/2010 | Jenkins ................. A61B 5/415 600/411 |
| 2013/0303890 A1 | 11/2013 | Duindam |
| 2016/0239963 A1* | 8/2016 | Kariv .................... A61B 6/481 |
| 2017/0172662 A1 | 6/2017 | Panescu et al. |
| 2017/0231714 A1 | 8/2017 | Kosmecki et al. |
| 2019/0000563 A1 | 1/2019 | Schneider et al. |

* cited by examiner

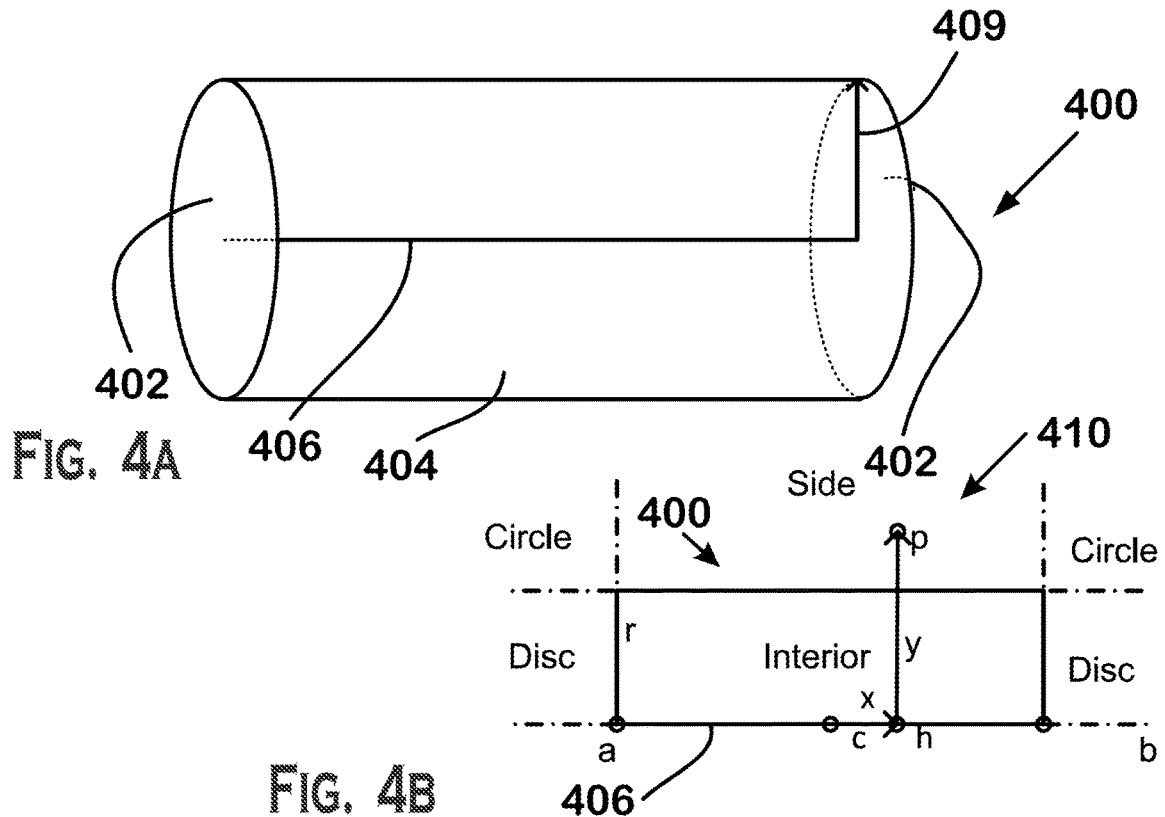
FIG. 4A
FIG. 4B
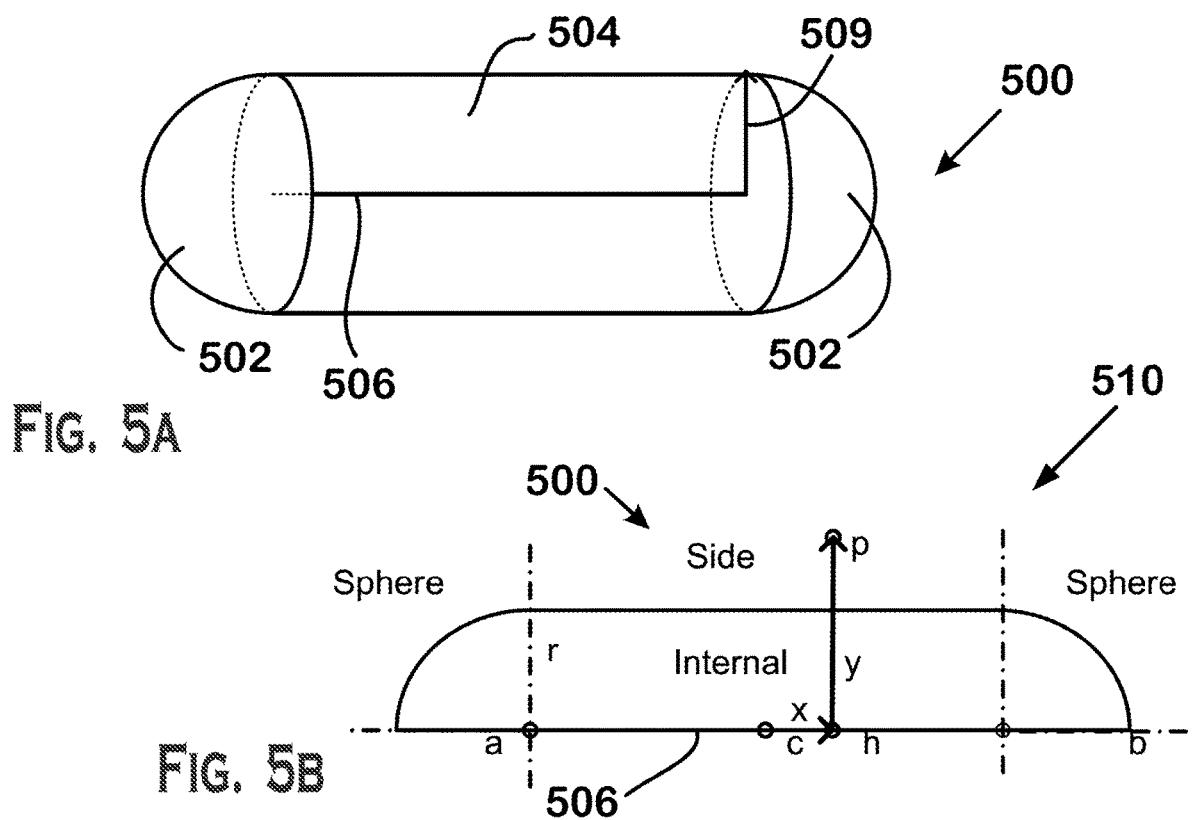
FIG. 5A
FIG. 5B

MONITORING DISTANCE TO SELECTED ANATOMICAL STRUCTURES DURING A PROCEDURE

BACKGROUND

Physicians utilize various surgical instruments when performing surgical procedures. There is a possibility that the surgical instrument being used can cause injury to the anatomy when the instrument unintentionally reaches certain critical regions of the anatomy such as nerves, blood vessels, brain and others. There is value in automatically alerting the user when the surgical instrument comes near such critical anatomical structures. During the procedure, nearby anatomical structures unrelated to the procedure should be avoided if possible.

SUMMARY

A method for monitoring proximity of an instrument to a monitored anatomical structure of a subject is provided. The method includes determining location of an instrument, determining distance of the instrument to the monitored anatomical structure, and determining whether the distance of the instrument to the monitored anatomical structure is below a threshold. If the distance is below the threshold, then a warning is generated and output. If the distance is not below the threshold, then no warning is generated.

A system for monitoring proximity of an instrument to a monitored anatomical structure of a subject is provided. The system includes an output device, an instrument, and a workstation. The workstation is configured to determine a location of the instrument, determine distance of the instrument to the monitored anatomical structure, and determine whether the distance is below a threshold. If the distance is below a threshold, the workstation generates and outputs a warning via the output device and if the distance is not below the threshold, then the workstation does not generate the warning.

A non-transitory computer-readable medium is also provided. The non-transitory computer-readable medium stores instructions that, when executed by a processor, causes the processor to monitor proximity of an instrument to a monitored anatomical structure of a subject by determining location of an instrument, determining distance of the instrument to the monitored anatomical structure, and determining whether the distance of the instrument to the monitored anatomical structure is below a threshold. If the distance is below the threshold, then a warning is generated and output. If the distance is not below the threshold, then no warning is generated.

BRIEF DESCRIPTION OF THE DRAWINGS

A more detailed understanding can be had from the following description, given by way of example in conjunction with the accompanying drawings wherein:

FIGS. 4A-7B illustrate four different geometric primitives for assisting with determining distance from an instrument to a monitored anatomical structure, according to an example.

DETAILED DESCRIPTION

Figure 1:
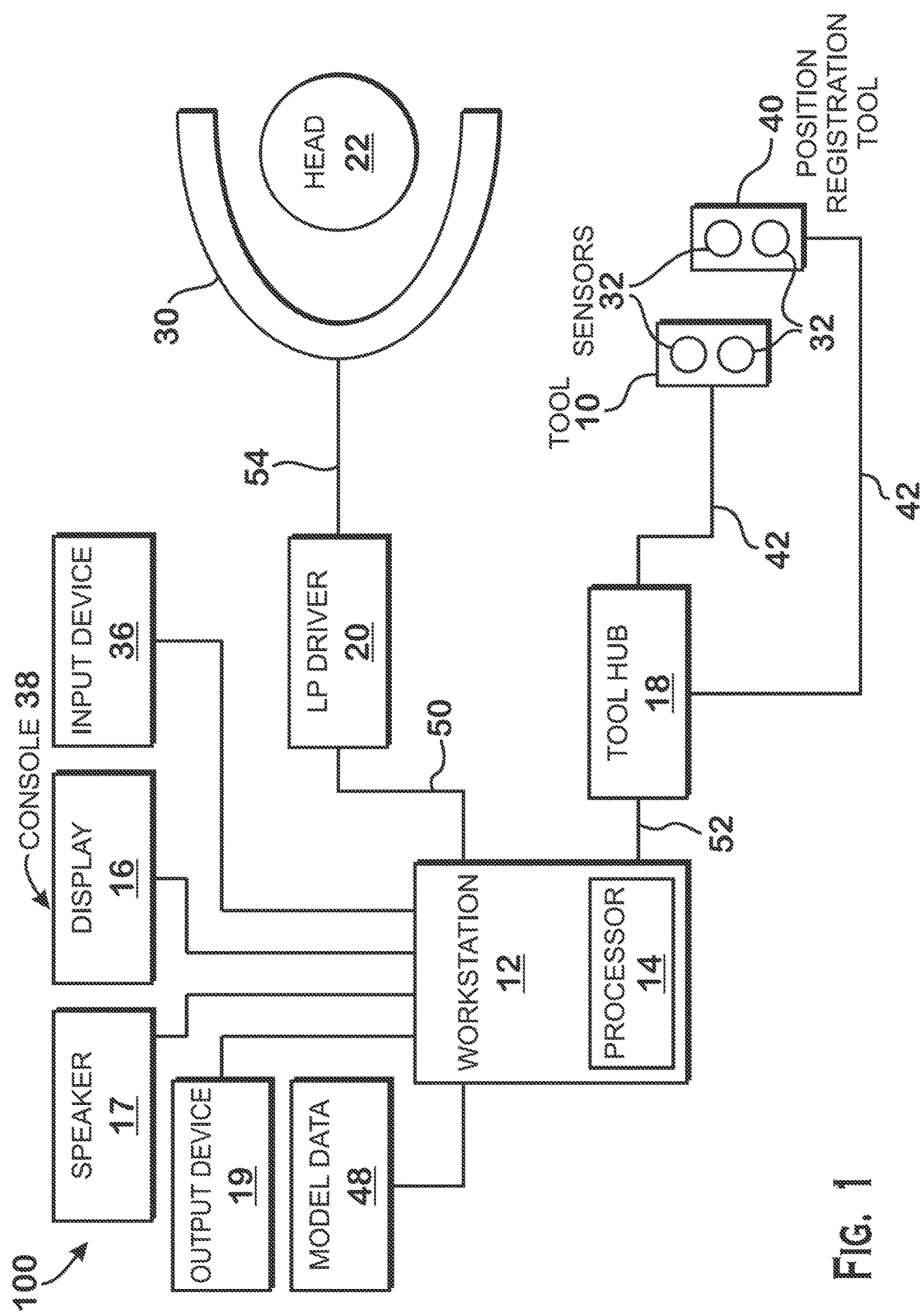
FIG. 1 is a schematic overview of an instrument location tracking system according to an example.

Physicians performing invasive procedures utilize instruments inserted into a human body to perform the procedures. Such procedures typically involve actions to be performed on specific targeted anatomical structures. During the procedure, nearby anatomical structures unrelated to the procedure should generally be avoided.

A system and techniques are provided herein for monitoring the position of such unrelated nearby anatomical structures (also referred to as "monitored anatomical structures" herein) relative to one or more surgical instruments. The system emits a warning to a human operator such as a surgeon if one of the instruments is too close to a monitored anatomical structure.

The system includes several components: sensors on the instruments, a location pad for emitting signals for determining location of the sensors, and a workstation that interfaces with the location pad and the sensors and also has data representing a three-dimensional model of the subject that has been "registered" to the location pad. The location pad includes a number of field generators that generate and emit fields to be sensed by the sensors on the surgical instruments. The sensors receive these signals and transmit the signals to the workstation for processing. The workstation analyzes the signals to determine position of the sensors relative to the field generators of the location pad. A pre-procedure registration procedure correlates the location of a subject expressed relative to the field generators of the location pad to a 3D model of the subject that can be obtained using medical imaging techniques such as a computerized tomography (CT) scan or a magnetic resonance imaging (MRI) scan. This registration procedure is performed by moving a registration instrument including a sensor in the vicinity of a subject while indicating the corresponding location within the 3D model of that subject. The registration procedure thus correlates points in space relative to the location pad (i.e., points in reality) with points in the 3D model, thereby correlating points on the physical subject to points in the 3D model of that subject. This correlation allow for a correlation between the sensors (and thus the instruments), whose locations are determined relative to the location pad, and the 3D model. With the positions of the instruments defined in the space of the 3D model, the workstation is able to calculate distance of the instruments to the monitored anatomical structures represented within that 3D model and to provide a warning if an instrument is found to be too close to a monitored anatomical structure.

One previous technology related to the present disclosure is the CARTO™ system, produced by Biosense Webster, Inc. (Diamond Bar, Calif.). Aspects of the CARTO™ system and of other related technologies can be found in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, which disclosures are all incorporated herein by reference.

FIG. 1 is a schematic overview of an instrument location tracking system 100 in accordance with an embodiment of the present invention. As shown in FIG. 1, the system comprises one or more medical instruments 10 (e.g., catheter, guidewire, endoscope, or the like), a console 38 comprising at least a workstation 12 comprising at least a processor 14 and one or more display devices 16 (such as a monitor), an instrument hub 18, a location pad 30, a position registration instrument 40, and a location pad driver ("LP driver") 20.

The workstation 12 is configured to communicate via a link 50 with the LP driver 20 to cause the LP driver 20 to drive field generators within the location pad 30. The field generators emit field signals (e.g., electromagnetic or other type of fields such as acoustic) that are detected by the sensors 32. The sensors 32 generate response signals in response to the field signals. The response signals are received by the instrument hub 18. The instrument hub 18 communicates with sensors 32 on the instrument(s) 10 and position registration instrument 40 via communication links 42. Communication links 42 may be wired or wireless links. The instrument hub 18 transmits the response signals or processed versions of the response signals to the workstation 12 via link 52, which may be a wired or wireless link.

The workstation 12 determines position and orientation of the sensors 32, and thus of the objects the sensors 32 are incorporated within or attached to (e.g., the instrument(s) 10) based on characteristics of the response signals. In one example, the field generators in the location pad 30 each have known locations. The sensors 32 receive signals from multiple field generators of the location pad 30. The signals received from different field generators can be differentiated based on time (e.g., different field generators are driven at different times so that the time at which the sensors 32 receive signals can be correlated to different field generators), frequency (e.g., different field generators are driven with signals of different frequencies so that the frequency of the signal received by the sensors 32 identifies individual field generators), or based on other characteristics of the signals generated by the field generators.

As described above, the instrument hub 18 transmits the signals (or processed versions of the signals) received from the sensors 32 to the workstation 12 for processing. The workstation 12 processes the signals to determine the location of the sensors 32 relative to the field generators of the location pad 30. The processing that is done to determine the locations of the sensors 32 depends on the type of signal emitted by the field generators. In some examples, the processing determines amplitudes of the signals received in response to each of the field generators. A greater amplitude indicates a smaller distance to the field generator and a lower amplitude indicates a greater distance to the field generator. With distance determinations for multiple field generators per sensor 32 (e.g., 3), location relative to the field generators can be determined through triangulation. Alternatively, any technically feasible technique for determining location based on response to signals can be used.

As described above, the system 100 also includes a position registration instrument 40, which can be embodied as a handheld wand or in any other technically feasible manner. The position registration instrument 40 is used to correlate a three-dimensional model, stored in model data 48, with the locations of the field generators in the location pad in a registration procedure. In one example, the 3D model of the model data 48 is a computer data representation of the operation subject (e.g., the head 22 of a patient). This 3D model may be obtained through medical imaging techniques such as a computerized tomography ("CT") scan or magnetic resonance imaging ("MRI"), or any other imaging technique that produces data that can be converted into a 3D model.

To perform the registration procedure, the position registration instrument 40 is placed (e.g., by a human operator such as a surgeon or automatically by an automated machine) at a particular location in the vicinity of the subject (e.g., the head 22). The workstation 12 then associates that position with a position within the 3D model stored in the model data 48, thereby correlating a point in the 3D model to a point in reality (as defined relative to the field generators of the location pad 30). This association may be made in response to a specific indication by an operator such as a surgeon. In such a scenario, the workstation 12 displays the 3D model from the model data 48 on the display 16. The operator moves the position registration instrument 40 to a particular location, and then indicates to the workstation 12 the corresponding location in the 3D model via the input device 36.

In an alternative scenario, the workstation 12 automatically associates locations in real space with locations in the 3D model. In one example, this automatic association is done as follows. The position registration instrument 40 is moved around the vicinity of the operation subject (e.g., the head 22). The workstation 12 processes data received from the position registration instrument 40 to identify the corresponding location in the 3D model. In one example, the position registration instrument 40 includes a camera and the workstation 12 performs image processing on images received with the position registration instrument 40 to identify the location of the position registration instrument 40 in the 3D model. In some examples, multiple points of correlation between real space (e.g., defined relative to the field generators of the location pad 30) and the 3D model are obtained and stored to improve the accuracy of the registration and to achieve rotational, as well as positional, registration. More specifically, the position registration instrument 40 is moved to multiple locations in the vicinity of the subject (e.g., head 22) and for each such location, the workstation 12 correlates the location of the position registration instrument 40 (as indicated by the sensor(s) 32 attached to the position registration instrument 40) with specific locations in the 3D model of the head. Although the position registration instrument 40 is described as the instrument being used to achieve registration of positions between real space and the 3D model, any other instrument, including instruments used for other purposes may alternatively be used.

Figure 2:
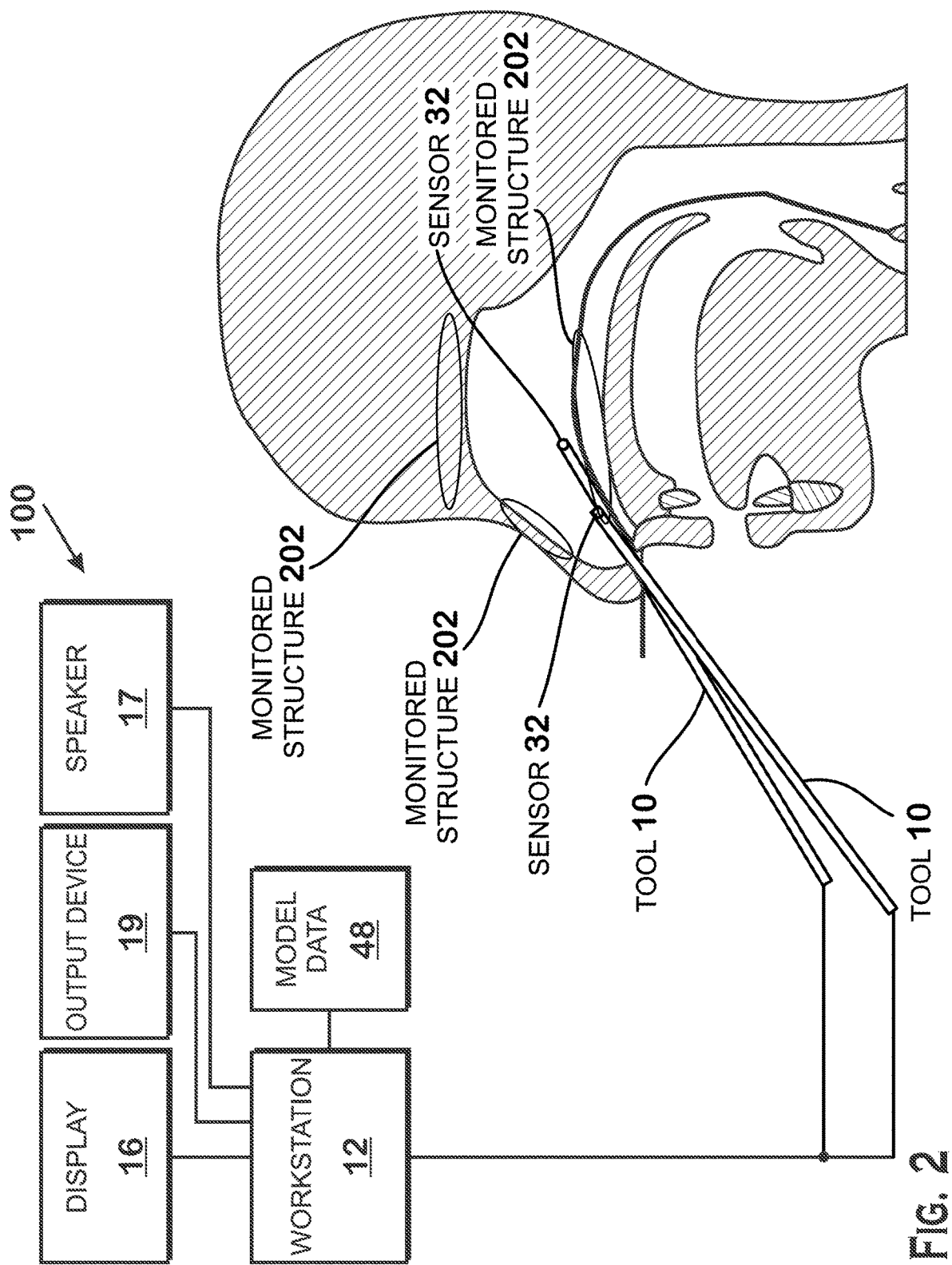
FIG. 2 is a schematic diagram illustrating aspects of the system, including aspects related to monitoring position of instruments relative to example monitored anatomical structures, according to an example.

With the 3D model of the head registered to the subject (e.g., head 22), the workstation 12 is able to monitor the position of instruments 10 relative to anatomical structures of the subject (e.g., head 22). Such monitoring can be used for a variety of purposes, such as to prevent contact with anatomical structures deemed not involved in a particular procedure or deemed to be vulnerable or susceptible to being damaged by an instrument 10. FIG. 2 is a schematic diagram illustrating aspects of the system 100, including aspects related to monitoring position of instruments 10 relative to example monitored anatomical structures 202 (also simply "monitored structures 202").

The instruments 10 illustrated include sensors 32 attached thereto. The workstation 12 monitors the location of the instruments 10 (via the location pad 30 as described with respect to FIG. 1). Several monitored structures 202 are illustrated. The workstation 12 determines the distance from the instruments to the monitored structures 202. If the distance to any particular instrument 10 is below a threshold, the workstation 12 triggers a warning to be output through the speaker 17, the display 16, and/or another output device 19. The distance of a particular instrument 10 to a monitored structure 202 being below the threshold may be referred to herein as the particular instrument 10 being too close to the monitored structure 202.

One or more aspects of the warning may be dependent on the distance of the instrument 10 to a particular monitored structure 202. In one example, in response to the instrument 10 being moved too close to a monitored structure 202, the workstation 12 causes the speaker 17 to repeatedly emit a beeping sound. In such an example, as the instrument 10 is moved closer to a monitored structure 202, the workstation 12 makes the beeps one or both of louder or closer together in time and as the instrument 10 is moved farther away from the monitored structure 202, the workstation 12 makes the beeps one or both of softer or spaced farther apart.

In another example, in response to the instrument 10 being moved too close to a monitored structure 202, the workstation 12 causes a visual indicator to be displayed on the display 16. As the instrument 10 is brought closer to the monitored structure 202, an aspect of the visual indicator is modified. In an example, as the instrument 10 is brought closer to the monitored structure 202, the visual indicator is made brighter, bigger, and/or is made to have a higher intensity of a particular color and as the instrument 10 is brought farther from the monitored structure 202, the visual indicator is made less bright, smaller, and/or is made to have a lower intensity of a particular color. Although some types of warnings are described, it should be understood that any warning may be used and that any type of variation of that warning could be used to indicate distance between the instrument 10 and the monitored structure 202.

The monitored structures 202 may be included by a human operator into the 3D model in the model data 48. To do this, a human operator would view the 3D model on a computer system such as workstation 12 and would indicate with an input device the structures to be monitored. The computer system would then add such indications into the 3D model for use for monitoring distance during a procedure. As described above, during the procedure, the workstation 12 tracks the location of the instrument 10 relative to monitored structures 202 and generates warnings when such instruments are deemed to be too close to a monitored structure 202.

Although the system described as performing the location tracking and monitoring is described as being the system that performs the registration, it is also possible for the two systems to be different systems. A system other than system 100 could be used to perform the registration. Also, although a head is shown and described as the anatomy involved in a procedure, it is possible to utilize the techniques described herein for any part of human anatomy.

The display 16 can be a traditional display or can be virtual reality glasses. The virtual reality glasses may have appropriate shielding, such as X-ray shielding provided by lead, if a procedure involves imaging appropriate for such shielding. The display 16 may also be a remote display (i.e., a display remotely located from the patient), which could facilitate remote surgery along with remotely controlled instruments 10.

Figure 3:
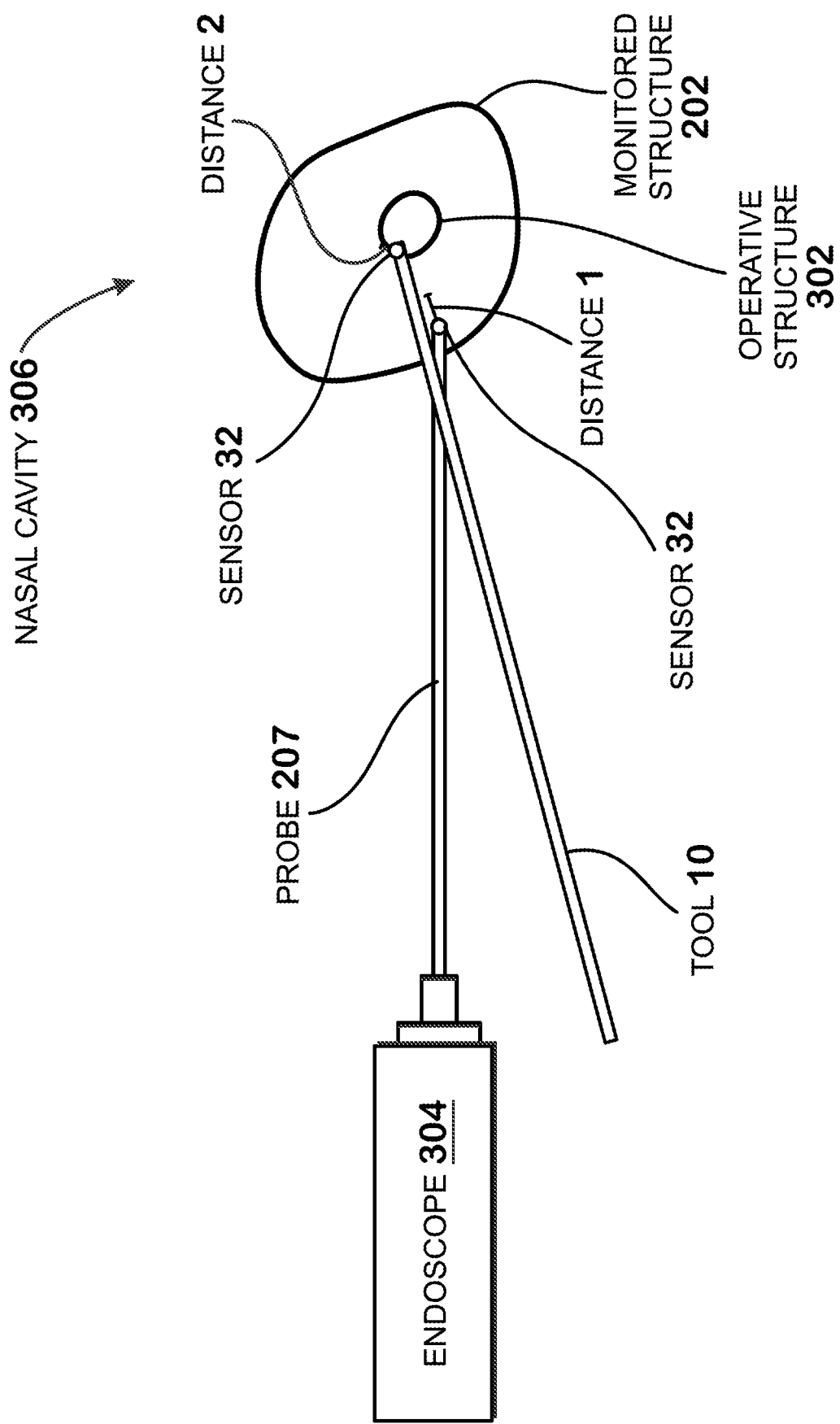
FIG. 3 illustrates an example of a use of monitoring for proximity to a monitored structure.

FIG. 3 illustrates an example of a use of monitoring for proximity to a monitored structure 202. An endoscope 304 is used to view inside a nasal cavity 306. The endoscope 304 has a probe 207 with a sensor 32. Using the location pad 30, the workstation 12 monitors the location of the probe 207 with respect to a monitored structure 202. An instrument 10 is used to operate on an operative structure 302, which may be a nasal polyp in an example. The monitored, non-operative structure 202 comprises tissue close to the operative structure 302 that should not be contacted significantly by the instrument 10.

During a procedure, the workstation 12 monitors the distance between the instrument 10 and the monitored structure 202 ("distance 2") and the distance between the probe 207 and the monitored structure 202 and emits a warning if the instrument 10 or probe 207 (or both) are too close to the monitored structure 202. The workstation 12 may vary the aspects (frequency, intensity, or other aspects) of the warning based on proximity of the instrument 10 or probe 207 to the monitored structure 202. Although a particular number and particular types of instruments are shown, the position of any instruments may be monitored with respect to monitored structures 202.

A set of techniques is now described for calculating distance from a sensor 32 to a monitored structure 202. In this set of techniques, the sensor 32 is considered to be a point. A monitored structure 202 is considered to be a collection of one or more geometric primitives. In one example, a monitored structure 202 is considered to include a collection of one or more geometric primitives selected from the set of a cylinder, a line-swept sphere, a cone, and a cone-sphere. To apply the monitoring technique in which distances between one or more sensors 32 and one or more monitored structures 202 are monitored, the workstation 12 (or another system) modifies the 3D model from the format generated based on a particular medical scan into a format in which at least some anatomical features are represented as a combination of the geometric primitives.

In one example, only structures that are monitored are converted to such a format. In other examples, additional anatomical features other than the monitored structures 202 are converted to such a format. In yet other examples, all structures of the 3D model are converted to such a format. In one example, this conversion is done automatically, via the workstation 12 or another system. In another example, this conversion is done manually, with an operator creating and compositing one or more such geometric primitives to form the parts of the 3D model to be represented in such a manner. In one example, the geometric primitives are created and composited to fully enclose the original structure in the 3D model that the geometry primitives are replacing. In other words, no portion of the original structure in the 3D model extend outside of the geometric primitives that replace that original structure, which provides a "conservative" distance measurement in that distance from such geometric primitive to an instrument is guaranteed to be at least as large as distance to the actual structure associated with that geometric primitive.

Figure 6A:
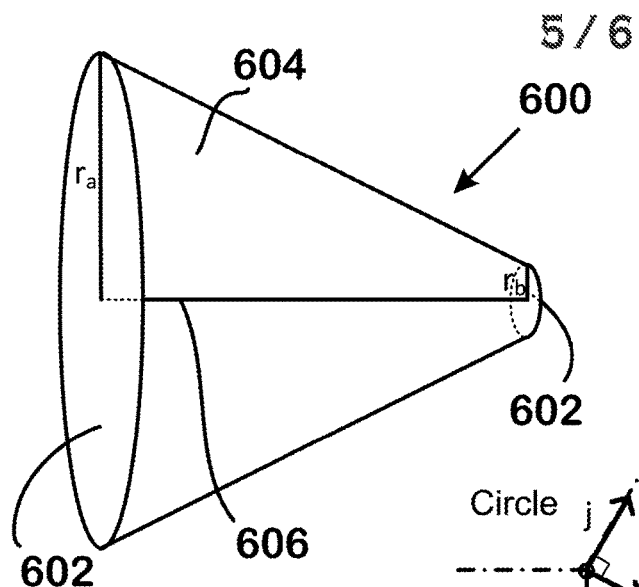
Figure 6B:
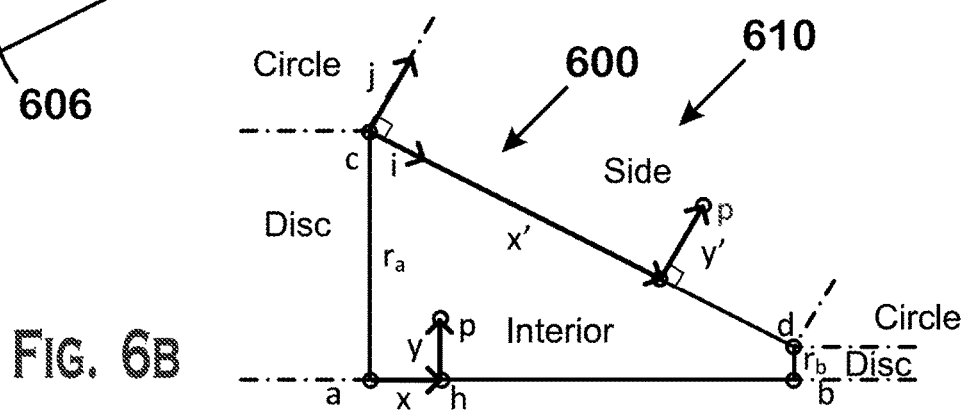
Figure 7A:
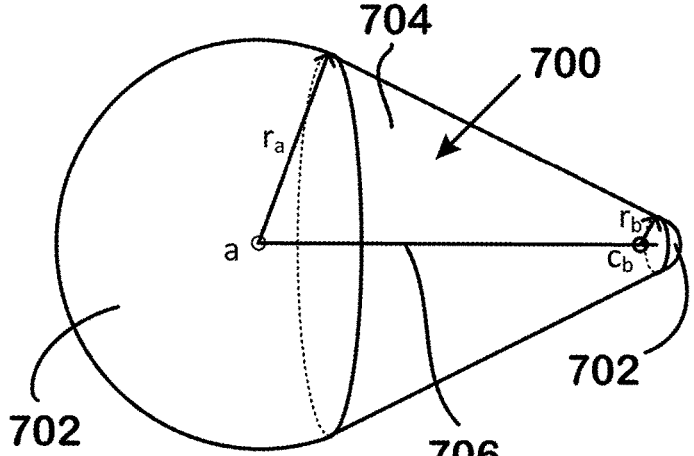
Figure 7B:
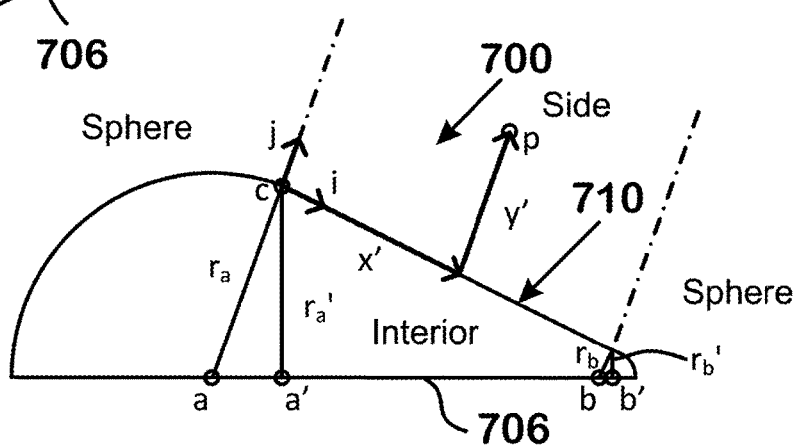

Some example techniques for determining distance between a sensor 32 and a geometric primitive are now provided with respect to FIGS. 4A-7B. FIGS. 4A-7B illustrate four different geometric primitives: a cylinder (FIGS. 4A-4B), a line-swept sphere (FIGS. 5A-5B), a cone (FIGS. 6A-6B), and a cone-sphere (FIGS. 7A-7B). Each of these geometric primitives is a rotation of a particular two-dimensional shape around a central axis. FIGS. 4A, 5A, 6A, and 7A illustrate the three-dimensional geometric primitives and FIGS. 4B, 5B, 6B, and 7B illustrate the corresponding two-dimensional shapes that are rotated around an axis to obtain the three-dimensional geometric primitives. The techniques described herein to determine distance may be performed by the workstation 12 in response to the instruments 10 being detected as moving or can be performed periodically.

FIG. 4A illustrates an example cylindrical geometric primitive 400. The cylindrical geometric primitive 400 includes two circular faces 402 and a cylindrical side 404. The radius 409 of the cylinder 400 is also shown. As described above, the cylindrical geometric primitive 400 comprises a rectangular shape rotated around the central axis 406. FIG. 4B illustrates aspects of this rectangular shape 410, including aspects related to calculating the distance from a point "p" to the cylinder 400, according to an example.

In FIG. 4B, the axis 406 around which the rectangle 410 is rotated is defined as the line segment between points a and b (referred to as "line segment ab" or just "ab"). Radius r (corresponding to radius 409 in FIG. 4A) is shown. Point c is the center point of line segment ab. Determining distance to the cylinder depends on identifying which Voronoï region of the cylinder the point is in. A Voronoï region is a region in a plane whose geometry and position is based on the distance to points in a particular portion of the plane. In FIG. 4B, three Voronoï regions include the disc region, the circle region, and the side region. A point in the disc region is closest to the discs 402 of the cylinder 400. A point in the circle region is closest to the circle outlining the discs 402 in the cylinder 400. A point in the side region is closest to the side 404 of the cylinder 400. The interior region is a region in which a point is inside of the boundaries of the cylinder 400. Note, although point p is shown in a particular location, which is in the side region, the techniques below and the vectors and distances shown are calculated in the same manner if the point p falls in a different region (e.g., $n^2=(c-p)^2$ regardless of which region point p falls in), except where explicitly pointed out herein.

Determination of which region a particular point is in is performed based on certain vectors calculated based on the coordinates of the point and the coordinates of the cylinder 400. These vectors and the expressions provided below are defined within the plane that coincides with points a, b, and p. This signed distance along the axis x is defined as:

$$x=(c-p)\cdot u$$

where u is a unit vector along the axis 406, defined as:

$$u=(b-a)/\|b-a\|$$

where the double vertical line brackets indicate magnitude. Point h is the orthogonal projection of p onto the axis 406 as shown. l, which equals $\|b-a\|$, is the length of axis 406. The squared distance from vertex p to vertex c is $n^2=(c-p)^2$. y is the distance from point p to point h, which equals $\|p-h\|$. The squared distance $y^2=\|p-h\|^2$, also equals $n^2-x^2$.

Identification of the Voronoï region in which point p lies occurs as follows. If the magnitude of x, |x|, is less than ½, then the point is either in the interior region of the cylinder 400 or in the side region illustrated in FIG. 4B. If $y^2<r^2$ then p is inside the cylinder because its orthogonal projection on the axis 406 is less than ½ and the distance to the axis is less than the radius of the cylinder. If $y^2 \geq r^2$ then the point p is in the side region and the squared distance to the cylinder is $(y-r)^2$ and the distance to the cylinder is y-r.

If the magnitude of x, |x|, is greater than ½, then the point p is either in the circle or the disc region. If $y^2<r^2$, then the point p is in the disc region and the squared distance is $(|x|-½)^2$. If |x| is less than or equal to ½, then the point p is in the circle region and the squared distance is: $(y-r)^2+(|x|-½)^2$. Obviously, the distance can be obtained by performing a square root operation on the squared distances if needed. In some examples, for efficient operation, it is better to perform tests over the x coordinate before testing if $y^2<r^2$.

FIG. 5A illustrates an example line-swept sphere geometric primitive 500. The line-swept sphere geometric primitive 500 includes two semi-spherical faces 502 and a cylindrical side 504. The radius 509 of the line-swept sphere 500 is also shown. This radius is the radius of the cylindrical side 504 as well as of the semi-spherical faces 502. The line-swept sphere 500 comprises the shape 510 of a rectangle joined with two quarter circles, rotated around a central axis 506. FIG. 5B illustrates aspects of this shape 510, including aspects related to calculating the distance from point p to the line-swept sphere 500, according to an example.

In FIG. 5B, points a and b define the axis 506. Point a is the center of the left semi-circular sphere and point b is the center of the right semi-circular sphere. Radius r is also shown. The points and distances illustrated are similar to those described with respect to FIG. 4B. Point c is the center of line segment ab. Point h is the orthogonal projection of p onto ab. x is the distance from c to h and y is the distance from h to p. The following expressions define various relations within FIG. 5B:

$$x=(c-p)\cdot u$$

$$u=(b-a)/\|b-a\|$$

$$l=\|b-a\|$$

the squared distance from $p$ to $c$ is: $n^2=(c-p)^2$ $$y^2=\|p-h\|^2=n^2-x^2$$

If the projected point lies between a and b (i.e., |x|<½), then the point lies within either the side region or the internal region. If $y^2<r^2$ then point p is within the internal region and the distance from p to the line-swept sphere 500 is considered to be 0. If $y^2 \geq r^2$ then point p is within the side region and the distance from p to the line-swept sphere 500 is calculated as y-r, with the squared distance calculated as $(y-r)^2$.

If the projected point lies beyond a or b (i.e., |x|≥½) then p is either in the sphere region or the internal region. The squared distance to the end vertex of the cylinder (i.e., either a or b, also the center point of the semi-spherical faces 502), $m^2=y^2+(|x|-½)^2$. If $m^2<r^2$, then point p is within the shape 500 and the distance is 0. Otherwise, p is in the sphere region and the squared distance from the point p to the shape 500 is $(m-r)^2$ (i.e., the distance from the center of the semi-spherical face to the point minus the radius of the semi-spherical face, squared).

FIG. 6A illustrates an example conical geometric primitive 600. The conical geometric primitive 600 includes two circular faces 502 and a conical side 604. Two radii—$r_a$ and $r_b$—which are radii of the two different circular faces 502—are also shown. The conical geometric primitive 600 includes a right trapezoid shape rotated around the axis 606. FIG. 6B illustrates aspects of this right trapezoid shape 610, including aspects related to calculating the distance from a point p to the conical geometric primitive 600, according to an example.

In FIG. 6B, the axis 606 around which the right trapezoid is rotated is defined as the line segment ab. As with the above shapes, determining distance of point p to the cone depends on identifying which Voronoï region of the cone the point is located within. These regions include a disc region, a circle region, a side region, and an interior region, as shown in FIG. 6B. Several values and expressions are used herein for calculating the distance of p from the cone. One such value is δ, which is the difference between the two radii and equals $r_a - r_b$. Another value is s, which is the length of the side of the cone, and is expressed as:

$$(l^2 + \delta^2)^{1/2}$$

where l is the length of axis 606, equal to $\|b-a\|$.

The signed distance along the axis 606 is denoted as:

$$x = a - p \cdot u$$

where u is a unit vector along the axis 406, defined as:

$$u = (b-a)/\|b-a\|$$

The squared distance from point p to point a is:

$$n^2 = (a-p)^2$$

The squared distance from point p to the axis 606 is:

$$y^2 = \|p - h\|^2 = n^2 - x^2$$

Classification into Voronoï regions occurs as follows. If x<0, then the point p is either in the disc region to the left of radius $r_a$ or in the circle region above and to the left of the trapezoid. More specifically, if $y^2 < r_a^2$, then p is in the disc region and the squared distance from p to the cone 600 is $x^2$. If $y^2 \geq r_a^2$, then the squared distance from p to the cone 600 is calculated as the squared distance to the circle outlining the left-most disc, which equals $(y - r_a)^2 + x^2$.

If x is greater than or equal to zero, then point p is either in the side region, the interior region, or the right-side circle or disc regions. If $y^2 < r_b^2$, then the point p is either in the interior region or in the right-most disc region. If x>l, then p is in the disc region and the squared distance from point p to the cone 600 is $(x-l)^2$. If x≤l, then p is in the interior region and the distance between p and the cone is considered to be 0.

If x is greater than or equal to zero and $y^2$ is greater than nor equal to $r_b^2$, then distance calculation is somewhat more complicated and relies on additional values shown, such as i, j, x', and y'. These values represent values in a different coordinate frame in which the edge of the cone, represented by line segment cd, represents a horizontal axis and point c represents the origin. The orthonormal vectors of this coordinate frame, i and j, are calculated as follows:

$$i = \left(\frac{\delta}{s}, \frac{l}{s}\right)$$

$$j = \left(\frac{l}{s}, \frac{\delta}{s}\right)$$

One way to calculate the coordinates, x' and y', in this new coordinate frame is by calculating the distance between p and the line that defines the y axis of the new frame (i.e., the line that extends through j) and the distance between p and the line that defines the x axis of the new frame (i.e., the line that extends through i), respectively. These distances can be calculated in any technically feasible manner.

If x'<0, then p is in the left circle region and the squared distance from p to the cone equals $(y - r_a)^2 + x^2$. If s<x', then p is in the right circle region and the squared distance from p to the cone equals $y'^2 + (x'-s)^2$. If s>x>0, then p is in the side region and the squared distance from p to the cone equals $y'^2$.

The order of tests described above may affect performance. For instance, in some embodiments, performance is increased by first checking tests of the x coordinates before computing the y' and x' coordinates. It is possible for the cone to have only one circular face, in which case $r_b$ would be 0. The expressions provided above work in that case as well.

FIG. 7A illustrates an example cone-sphere primitive 700. The cone-sphere 700 includes two spherical faces 702 and a conical side 704. A first radius $r_a$ is shown extending from the center $c_a$ of the left spherical face 702 to the surface of that spherical face 702 and a second radius $r_b$ is shown extending from the center $c_b$ of the right spherical face 702 to the surface of that spherical face 702. The cone-sphere primitive 700 comprises the shape of a right trapezoid combined with two circle portions rotated around axis 706. This combined shape is illustrated in FIG. 7B, which illustrate aspects of calculating the distance from a point p to the cone-sphere 700.

In FIG. 7B, the axis 706 around which the shape 710 is rotated to form the cone-sphere 700 is illustrated. In addition, FIG. 7B shows radius $r_a$ of the left sphere, radius $r_b$ of the right sphere, centers a and b of left and right spheres, respectfully, points a' and b', which are end points of a cone, and which extend perpendicularly from line segment ab to the point at which the spheres meet the cone's side, and x', y', i, and j, which are similar to the cone of FIG. 6B and which will be described in more detail below. In addition, four Voronoï regions are shown: a left and right sphere region, a side region, and an interior region. Several values and expressions are used herein for calculating the distance of p from the cone-sphere. One such value is δ, which is the difference between the two radii and equals $r_a - r_b$. Another value is l, which represents the distance from the two centers of the spheres, equal to $\|b-a\|$. A cone smoothly joins the two spheres if l>δ. In that case, s, which is the length of the conical side, is expressed as:

$$(l^2 - \delta^2)^{1/2}$$

The radii of the cone are shown as $r_a'$ and $r_b'$. $h_a$ and $h_b$ denote the distances between the vertices a and a' and b and b', respectively. Thus:

$$h_a = \frac{r_a \delta}{l}$$

$$h_b = \frac{r_b \delta}{l}$$

$$r_a' = \frac{r_a s}{l}$$

$$r_b' = \frac{r_b s}{l}$$

Distance computation from p to the cone-sphere rely on a rotated coordinate frame having an origin at point c and orthonormal vectors i and j:

$$i = \left(\frac{s}{l}, \frac{\delta}{l}\right)$$

$$j = \left(-\frac{\delta}{l}, \frac{s}{l}\right)$$

x' and y' are coordinates of p in this new coordinate frame and can be calculated in any technically feasible manner. If x'<0, then p is in the left sphere region. For determining distance, $n^2$ is the squared distance of p to a and equals $(p-a)^2$. If $n^2 > r_a^2$, then the squared distance is $(n - r_a)^2$. Otherwise, p is in the interior region and the distance of p to the cone-sphere is 0.

If x'>s, then p is in the right sphere region. In this instance, $n^2$ is the squared distance of p to b, which equals $(p-r_b)^2$. If $n^2 > r_b^2$, then the squared distance from p to the cone-sphere is $(n-r_b)^2$. Otherwise, p is in the interior region and the distance is 0.

If s>x'>0, then p is either in the interior region or the side region. If y'<0, then p is in the interior region and the distance is 0. If y'>0 then p is in the side region and the distance from p to the cone-sphere is $y'^2$.

In any of the above, the distances may be expressed as squared distance to speed calculation by not requiring square root operations. For distance checking between the sensors 32 and monitored structures 202, the distance to be checked could be expressed as a squared distance and then the determined distance would not need to be square rooted. Alternatively, the determined distance could be square rooted if the distance to be checked is expressed as a distance and not a squared distance.

The above presents examples of geometric primitives that could be used to model and/or enclose anatomical structures of the 3D model of model data 48 for the purposes of monitoring distance of a sensor 32 to a monitored structure 202. However, it should be understood that other types of geometric primitives could be used alternatively or additionally to model and/or enclose anatomical structures for monitoring distance to monitored structures 202. Any technically feasible primitive and any technically feasible technique for determining distance to such primitives may be used for monitoring distance of the sensors 32 to the monitored structures 202.

Figure 8:
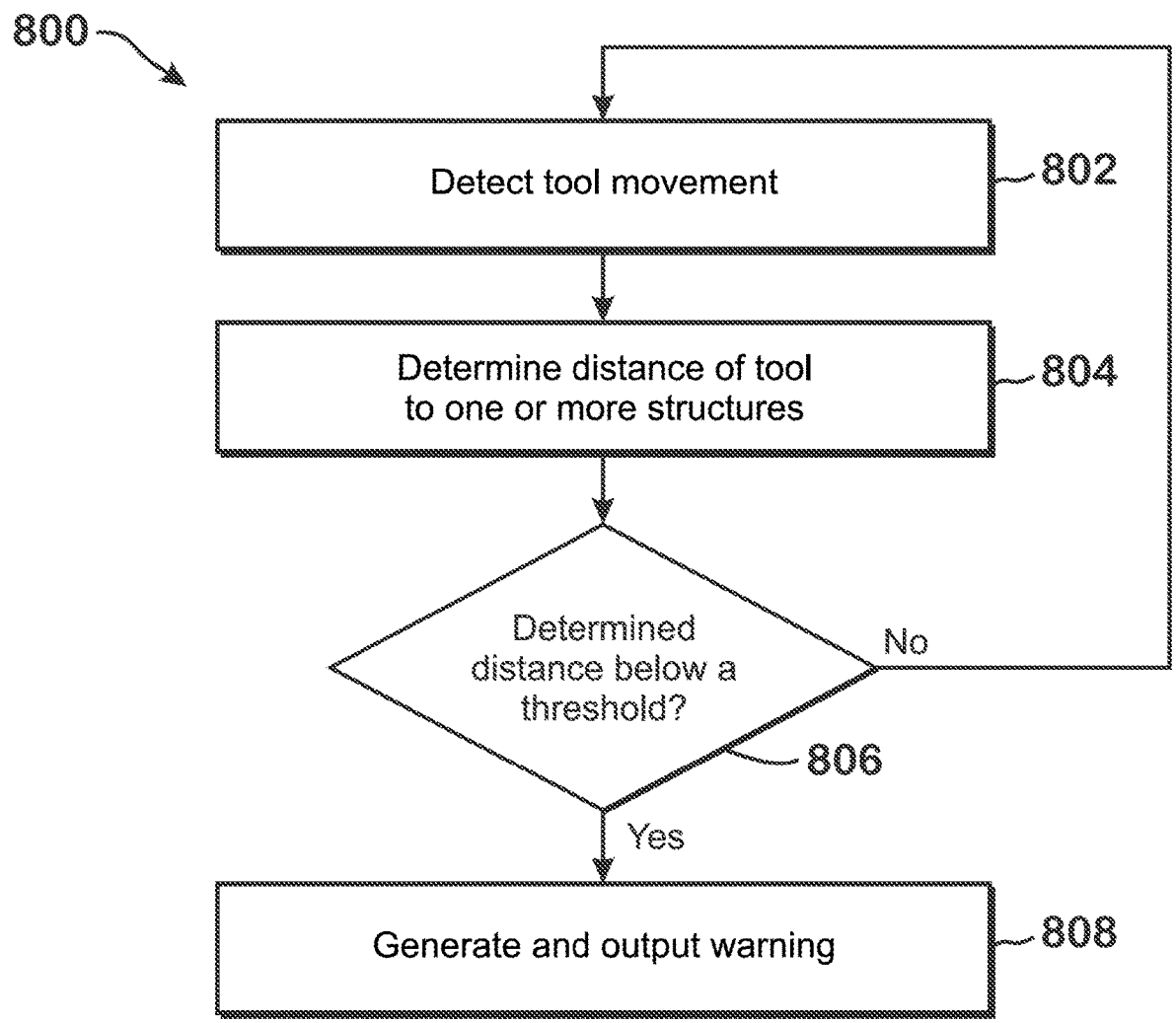
FIG. 8 is a flow diagram of a method for monitoring distance of an instrument to monitored structure, according to an example.

FIG. 8 is a flow diagram of a method 800 for monitoring distance of an instrument 10 to monitored structure 202, according to an example. Although described with respect to the system described in conjunction with FIGS. 1-7B, those of skill in the art will understand that any system configured to perform the method with any technically feasible order of steps falls within the scope of the present disclosure.

As shown, the method 800 begins at step 802, where the workstation 12 detects movement of an instrument 10. As described above, the workstation 12 drives field generators in a location pad 30 that emits signals sensed by sensors 32 on the instruments 10. The signals are received by the workstation 12, which processes the signals to determine distance between the field generators in the location pad 30 and the sensors 32, and derives location of the sensors 32 based on those distances.

As also described above, the location of the subject (e.g., head 22) is registered to the location of the field generators of the location pad 30 via a registration procedure described herein. This registration correlates points in reality as defined relative to the positions of the field generators and in the vicinity of the subject (i.e., a head 22) to a 3D model of that subject. Because it is possible to determine a location of a sensor 32 in reality, it is possible to link the location of sensors 32 to locations within the 3D model of the subject.

At step 804, the workstation 12 determines distance from an instrument 10 to one or more monitored structures 202 defined in the 3D model of the subject. As described above, each of the monitored structures 202 can be associated with one or more geometric primitives for determining distance to the monitored structure 202. The geometric primitives may be associated with the one or more monitored structures 202 automatically or manually (i.e., in response to a user input). The geometric primitives may approximate the corresponding structure in the original 3D model generated based on a medical scan or may be shaped and sized to completely enclose the corresponding structure such that no portion of the corresponding structure extends past the outside of the corresponding structure. Expressing the monitored structures 202 as one or more geometric primitives allows for quick and efficient distance calculation. If multiple geometric primitives exist in the model, then in some embodiments, the workstation 12 calculates distance to each of those geometric primitives. For efficiency, the workstation 12 may identify a bounding volume around the sensor 32 and only check distance for geometric primitives of the 3D model within the bounding volume, thereby limiting the number of geometric primitives against which a particular sensor 32 is checked. In other embodiments or situations, the workstation 12 determines distance to a monitored structure without using a geometric primitive as described herein. Such distance calculations may be more time-consuming than distance calculations described herein.

At step 806, the workstation 12 determines whether any particular distance is below a threshold considered to be too close. This threshold may be a global threshold, may be defined per monitored structure 202 or may be defined per geometric primitive. If the distance to any particular monitored structure 202 is below a threshold, then the method 800 proceeds to step 808 and if the distance is not below a threshold, then the method 800 returns to step 802. At step 808, the workstation 12 generates and outputs a warning. The warning may be any output type that can notify a human operator, such as a surgeon, of proximity detection. In some examples, the warning comprises a visual output, such as a blinking dot, a change in color, or any other visual output on a screen visible to the human operator. In other examples, the warning comprises an audio output, such as a beep or other noise. The warning may include more than one type of warning, for example both displaying a warning and emitting an audio warning. One or more aspects of the warning may vary based on the distance between the sensor and the monitored structure 202.

The methods provided include implementation in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements method described herein.

The methods or flow charts provided herein can be implemented in a computer program, software, or firmware incorporated in a non-transitory computer-readable storage medium for execution by a general purpose computer or a processor. Examples of non-transitory computer-readable storage mediums include a ROM, a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed is:

1. A method for monitoring proximity of an instrument to a monitored anatomical structure of a subject, the method comprising:
   determining, by a workstation including a processor, a location of the instrument in model space by correlating a location of one or more sensors in real space to a location of the instrument in model space;
   determining, by the workstation, a distance of the instrument to the monitored anatomical structure, the determining including:
      representing the monitored anatomical structure as a collection of one or more geometric primitives of a three-dimensional model in model space, at least one of the one or more geometric primitives represented as a two-dimensional shape rotated around an axis, the one or more geometric primitives including one or more of a cylinder, a line-swept sphere, a cone, and a cone-sphere, and
      calculating a distance between the location of the instrument in model space and one or more locations of the one or more geometric primitives, by analyzing a point associated with the instrument in model space within a space defined by the two-dimensional shape associated with one of the one or more geometric primitives represented as a two-dimensional shape rotated around an axis;
   determining, by the workstation, whether the distance of the instrument relative to the monitored anatomical structure is below one or more thresholds; and
   outputting, to an output device, a user interface indication indicating whether the distance is below or above the one or more thresholds.

2. The method of claim 1, wherein determining location of the instrument comprises:
   detecting aspects of signals detected by one or more sensors coupled to the instrument.

3. The method of claim 2, wherein determining location of the instrument comprises:
   determining one or more locations of the one or more sensors based on signals detected by the one or more sensors.

4. The method of claim 2, wherein detecting aspects of signals comprises:
   causing one or more field generators of a location pad to emit the signals for detection by the one or more sensors coupled to the instrument.

5. The method of claim 1, wherein determining location of the instrument comprises:
   detecting aspects of signals detected by the one or more sensors in known relative location to each other, the sensors configured to sense one or more signals generated by one or more transmitters coupled to the instrument.

6. The method of claim 5, wherein determining location of the instrument further comprises:
   determining one or more locations of the one or more transmitters based on signals detected by the one or more sensors.

7. The method of claim 1, wherein determining distance of the instrument to the monitored anatomical structure comprises:
   identifying one or more portions of a three-dimensional model including the monitored anatomical structure; and
   determining distance of the determined location of the sensor to the one or more portions of the three-dimensional model including the monitored anatomical structure.

8. The method of claim 7, wherein:
   the three-dimensional model is registered to locations defined relative to field generators of a location pad and thus to the subject.

9. The method of claim 1, wherein:
   generating the user interface indication comprises varying one or more aspects of the user interface indication based on the determined distance of the instrument to the monitored anatomical structure.

10. A system for monitoring proximity of an instrument to a monitored anatomical structure of a subject, the system comprising:
    an output device;
    an instrument; and
    a workstation configured to:
       determine location of the instrument in model space by correlating a location of a sensor in real space to a location of the instrument in model space;
       determine distance of the instrument to the monitored anatomical structure, the determining including:
          representing the monitored anatomical structure as a collection of one or more geometric primitives of a three-dimensional model in model space, at least one of the one or more geometric primitives represented as a two-dimensional shape rotated around an axis, the one or more geometric primitives including one or more of a cylinder, a line-swept sphere, a cone, and a cone-sphere, and, and
          calculating a distance between the location of the instrument in model space and one or more locations of the one or more geometric primitives, by analyzing a point associated with the instrument in model space within a space defined by the two-dimensional shape associated with one of the one or more geometric primitives represented as a two-dimensional shape rotated around an axis;
       determine whether the distance of the instrument relative to the monitored anatomical structure is below one or more thresholds; and
       provide a user interface indication indicating whether the distance is below or above the one or more thresholds.

11. The system of claim 10, wherein the workstation is configured to determine location of the instrument by:
    detecting aspects of signals detected by one or more sensors coupled to the instrument.

12. The system of claim 11, wherein the workstation is configured to determine location of the instrument by:
    determining one or more locations of the one or more sensors based on signals detected by the one or more sensors.

13. The system of claim 11, wherein the workstation is configured to detect aspects of signals by:
    causing one or more field generators of a location pad to emit the signals for detection by the one or more sensors coupled to the instrument.

14. The system of claim 10, wherein the workstation is configured to determine location of the instrument by:
    detecting aspects of signals detected by one or more sensors in known relative location to each other, the sensors configured to sense one or more signals generated by one or more transmitter coupled to the instrument.

15. The system of claim 10, wherein the workstation is configured to determine distance of the instrument to the monitored anatomical structure by:
- identifying one or more portions of a three-dimensional model including the monitored anatomical structure; and
- determining distance of the determined location of the sensor to the one or more portions of the three-dimensional model including the monitored anatomical structure.

16. The system of claim 14, wherein:
the three-dimensional model is registered to locations defined relative to field generators of a location pad and thus to the subject.

17. The system of claim 10, wherein:
the workstation is configured to vary one or more aspects of the user interface indication based on the determined distance of the instrument to the monitored anatomical structure.

18. A non-transitory computer-readable medium storing instructions that, when executed by a processor, cause the processor to monitor proximity of an instrument to a monitored anatomical structure of a subject by:
- determining a location of the instrument in model space by correlating a location of one or more sensors in real space to a location of the instrument in model space;
- determining distance of the instrument to the monitored anatomical structure, the determining including:
  - representing the monitored anatomical structure as a collection of one or more geometric primitives of a three-dimensional model in model space, at least one of the one or more geometric primitives represented as a two-dimensional shape rotated around an axis, the one or more geometric primitives including one or more of a cylinder, a line-swept sphere, a cone, and a cone-sphere, and, and
  - calculating a distance between a position of the instrument in model space and one or more locations of the one or more geometric primitives, by analyzing a point associated with the instrument in model space within a space defined by the two-dimensional shape associated with one of the one or more geometric primitives represented as a two-dimensional shape rotated around an axis;
- determining whether the distance of the instrument to the monitored anatomical structure is below one or more thresholds; and
- outputting a user interface indication indicating whether the distance is below or above the one or more thresholds.

19. The non-transitory computer-readable medium of claim 18, wherein determining location of the instrument comprises:
detecting aspects of signals detected by one or more sensors coupled to the instrument.

20. The non-transitory computer readable medium of claim 18, wherein determining location of the instrument comprises:
detecting aspects of signals detected by the one or more sensors in known relative location, from a transmitter or multiple transmitters coupled to the instrument.

* * * * *